United States Patent
Arai et al.

(10) Patent No.: US 10,667,744 B2
(45) Date of Patent: Jun. 2, 2020

(54) SKIN FUNCTION EVALUATION DEVICE AND SKIN EVALUATION METHOD

(71) Applicant: Panasonic Intellectual Property Corporation of America, Torrance, CA (US)

(72) Inventors: Toshiya Arai, Osaka (JP); Shinji Uchida, Osaka (JP)

(73) Assignee: Panasonic Intellectual Property Corporation of America, Torrance, CA (US)

( * ) Notice: Subject to any disclaimer, the term of this patent is extended or adjusted under 35 U.S.C. 154(b) by 496 days.

(21) Appl. No.: 14/900,863

(22) PCT Filed: Jun. 20, 2014

(86) PCT No.: PCT/JP2014/003328
§ 371 (c)(1),
(2) Date: Dec. 22, 2015

(87) PCT Pub. No.: WO2014/208067
PCT Pub. Date: Dec. 31, 2014

(65) Prior Publication Data
US 2016/0135730 A1   May 19, 2016

(30) Foreign Application Priority Data

Jun. 28, 2013 (JP) ................. 2013-136185

(51) Int. Cl.
*A61B 5/00* (2006.01)
(52) U.S. Cl.
CPC ............ *A61B 5/442* (2013.01); *A61B 5/0077* (2013.01); *A61B 5/443* (2013.01); *A61B 5/444* (2013.01); *A61B 5/742* (2013.01); *A61B 5/743* (2013.01)

(58) Field of Classification Search
CPC ......... A61B 5/442; A61B 5/444; A61B 5/742; A61B 5/743; A61B 5/443; A61B 5/0077
See application file for complete search history.

(56) References Cited

U.S. PATENT DOCUMENTS 6,088,392 A * 7/2000 Rosenberg ........... H04N 19/176
375/240.03
2003/0063801 A1   4/2003 Rubinstenn
(Continued)

FOREIGN PATENT DOCUMENTS

CN   101911118 A   12/2010
FR   2 952 519 A1   5/2011
(Continued)

OTHER PUBLICATIONS

Extended European Search Report dated Jun. 3, 2016 for corresponding European Application No. 14817805.6.
(Continued)

*Primary Examiner* — Jacqueline Cheng
*Assistant Examiner* — Tho Q Tran
(74) *Attorney, Agent, or Firm* — Renner, Otto, Boisselle & Sklar, LLP

(57) ABSTRACT

An evaluation method for determining a skin sensory evaluation value from an image, including: acquiring an image of an area including skin of a subject; extracting a skin region from the image; calculating at least two characteristic indices representing characteristics of the image of the skin region; and determining a skin sensory evaluation value based on the calculated at least two characteristic indices.

14 Claims, 10 Drawing Sheets

(56) References Cited

U.S. PATENT DOCUMENTS

| | | | |
|---|---|---|---|
| 2003/0065523 A1* | 4/2003 | Pruche | A45D 44/005 382/118 |
| 2003/0065552 A1* | 4/2003 | Rubinstenn | A45D 44/005 705/26.7 |
| 2006/0216254 A1* | 9/2006 | Majmudar | A61K 36/9062 424/62 |
| 2007/0190175 A1* | 8/2007 | Cummins | A61K 8/23 424/618 |
| 2008/0304736 A1* | 12/2008 | Nakagawa | A61B 5/0059 382/165 |
| 2009/0196475 A1* | 8/2009 | Demirli | A61B 5/441 382/128 |
| 2009/0201365 A1 | 8/2009 | Fukuoka | |
| 2009/0245603 A1* | 10/2009 | Koruga | A45D 44/00 382/128 |
| 2010/0249731 A1 | 9/2010 | Stamatas | |
| 2010/0272333 A1 | 10/2010 | Stephan et al. | |
| 2010/0284610 A1 | 11/2010 | Yoshikawa | |
| 2014/0205159 A1 | 7/2014 | Yoshida | |
| 2014/0328509 A1* | 11/2014 | Guissin | G06T 5/002 382/100 |

FOREIGN PATENT DOCUMENTS

| | | |
|---|---|---|
| JP | 2003-024306 A | 1/2003 |
| JP | 2003-187251 A | 7/2003 |
| JP | 2006-142005 A | 6/2006 |
| JP | 2007-252891 A | 10/2007 |
| JP | 4105554 B2 | 4/2008 |
| JP | 2012-053813 A | 3/2012 |
| KR | 10-1076307 B1 | 10/2011 |
| WO | WO 2013/042436 A1 | 3/2013 |

OTHER PUBLICATIONS

International Search Report for corresponding International Application No. PCT/JP2014/003328 dated Sep. 16, 2014.

Chinese Search Report for corresponding Chinese Application No. 201480036117.3 dated Jan. 29, 2018.

Chinese Office Action and Chinese Search Report (with English translation thereof) for corresponding Chinese patent application No. 201480036117.3, dated Mar. 18, 2019.

\* cited by examiner (a)

(b)

(c)

(a)

(b)

(a)

(b)

(a)

(b)

(c)

(d)

CLARITY BY SUBJECTIVE EVALUATION

CLARITY BY SUBJECTIVE EVALUATION

SKIN FUNCTION EVALUATION DEVICE AND SKIN EVALUATION METHOD

TECHNICAL FIELD

The present application relates to an evaluation device and an evaluation method that determine a sensory evaluation value such as skin clarity or the like.

BACKGROUND ART

In the beauty industry, a device that measures a state of skin is desired. For example, a device that measures blemishes or wrinkles of skin has been realized. A device that measures such a physical characteristic amount of skin and also a sensory evaluation value such as skin clarity or the like is now desired.

For example, Patent Document 1 discloses a method for evaluating local skin clarity by putting a probe into contact with, or close to, the skin.

CITATION LIST

Patent Literature

Patent Document 1: Japanese Patent No. 4105554

SUMMARY OF INVENTION

Technical Problem

The clarity found by the method disclosed in Patent Document 1 is local skin clarity, and is not the clarity found from a wide region such as, for example, the entire cheeks of a face. Such local skin clarity does not match the skin clarity perceived from the entire face.

A non-limiting illustrative embodiment of the present application provides a sensory evaluation device and a skin evaluation method that determine a skin sensory evaluation value.

Solution to Problem

An evaluation method in an embodiment in the subject application is an evaluation for determining a skin sensory evaluation value from an image, including (a) acquiring an image of an area including skin of a subject; (b) extracting a skin region from the image; (c) calculating at least two characteristic indices representing characteristics of the image of the skin region; and (d) determining a skin sensory evaluation value based on the calculated at least two characteristic indices.

Advantageous Effects of Invention

The sensory evaluation device and the skin evaluation method disclosed in the present application determine a skin sensory evaluation value at high precision by use of at least two characteristic indices of an image of skin.

DESCRIPTION OF EMBODIMENTS

Figure 1:
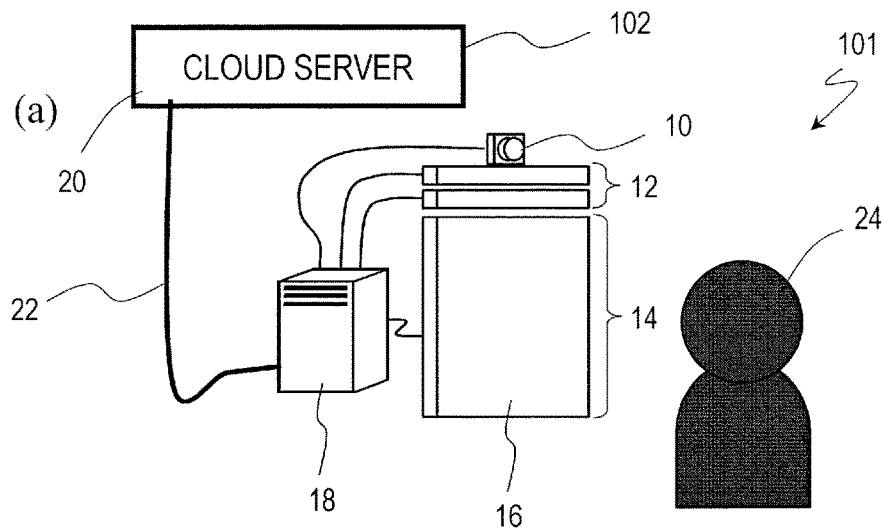
FIG. 1(a) schematically shows a structure of a sensory evaluation device for skin in an embodiment.
FIG. 1(b) shows a structure of a control device of the sensory evaluation device.
FIG. 1(c) shows a structure of a cloud server.
Figure 1:
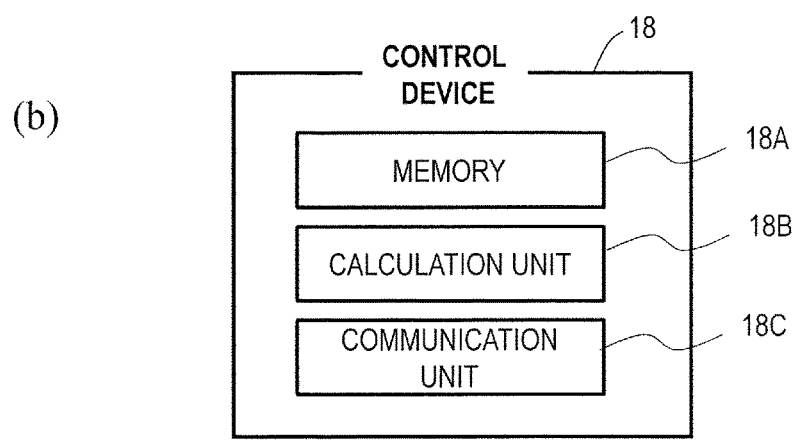
Figure 1:
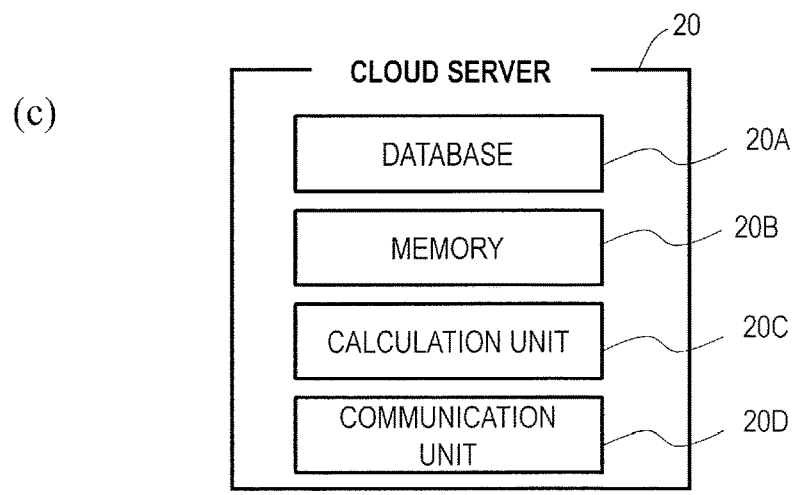

An overview of a sensory evaluation device for skin and an evaluation method for skin in an embodiment according to the present invention is as follows.

An evaluation method for determining a skin sensory evaluation value from an image in an embodiment according to the present invention includes (a) acquiring an image of an area including skin of a subject; (b) extracting a skin region from the image; (c) calculating at least two characteristic indices representing characteristics of the image of the skin region; and (d) determining a skin sensory evaluation value based on the calculated at least two characteristic indices.

In the step (b), the skin region may be divided into a plurality of unit blocks; in the steps (b) and (c), the at least two characteristic indices may be calculated to determine the skin sensory evaluation value on a unit block-by-unit block basis; and the evaluation method may further include (e) displaying, on a display device, the skin sensory evaluation value, found on a unit block-by-unit block basis, in association with a position of each of the unit blocks.

The step (b) may detect a face of the subject in the image, and remove areas of face parts from the image based on a position of the detected face to extract the skin region.

The step (e) may display, on the display device, the skin sensory evaluation value found on a unit block-by-unit block basis with a color tone or a gray scale suitable to the skin sensory evaluation value in association with the position of the corresponding unit block.

Each of the characteristic indices may be one selected from the group consisting of blemishes, wrinkles, texture and pores of the skin; nasolabial folds of the face; an average, a dispersion and hue of pixel values in the unit block; reflectance, water content, oil content and color unevenness at a surface of the skin.

The sensory evaluation value may be one selected from the group consisting of clarity of the skin, skin age of the subject, and impression of the skin of the subject.

The step (d) may determine the skin sensory evaluation value based on a correlation between the at least two characteristic indices measured on a plurality of subjects in advance and the sensory evaluation values determined by an evaluation performed on the skin of the plurality of subjects.

The correlation may be found by multiple regression analysis.

Information on beauty equipment or cosmetics regarding each of the calculated characteristic indices or the determined sensory evaluation value may be further displayed on a display device.

A sensory evaluation device in an embodiment according to the present invention includes an image capturing unit acquiring an image of an area including skin of a subject; a skin region extraction unit extracting a skin region from the image; a characteristic index calculation unit calculating at least two characteristic indices representing characteristics of the image of the skin region; and a sensory evaluation value determination unit determining a skin sensory evaluation value based on the calculated at least two characteristic indices.

The sensory evaluation device may further include a display unit. The skin region extraction unit may divide the skin region into a plurality of unit blocks; the characteristic index calculation unit may calculate the at least two characteristic indices on a unit block-by-unit block basis; the sensory evaluation value determination unit may determine the skin sensory evaluation value on a unit block-by-unit block basis; and the display device may display the skin sensory evaluation value, found on a unit block-by-unit block basis, in association with a position of each of the unit blocks.

The skin region extraction unit may detect a face of the subject in the image, and remove areas of face parts from the image based on a position of the detected face to extract the skin region.

The display unit may display the skin sensory evaluation value found on a unit block-by-unit block basis with a color tone or a gray scale suitable to the skin sensory evaluation value in association with the position of the corresponding unit block.

Each of the characteristic indices may be one selected from the group consisting of blemishes, wrinkles, texture and pores of the skin; nasolabial folds of the face; an average, a dispersion and hue of pixel values in the unit block; reflectance, water content, oil content and color unevenness at a surface of the skin.

The sensory evaluation value may be one selected from the group consisting of clarity of the skin, skin age of the subject, and impression of the skin of the subject.

The sensory evaluation value determination unit may determine the skin sensory evaluation value based on a correlation between the at least two characteristic indices measured on a plurality of subjects in advance and the sensory evaluation values determined by an evaluation performed on the skin of the plurality of subjects.

The correlation may be found by multiple regression analysis.

The display unit may further display information on beauty equipment or cosmetics regarding each of the calculated characteristic indices or the determined sensory evaluation value.

A sensory evaluation device in another embodiment according to the present invention includes an image capturing device; a control device including a storage element and a computation element; a display device; and a program stored on the storage element and structured to be executable by the computation element. The program (a) causes an image of an area including skin of a subject to be acquired; (b) causes a skin region to be extracted from the image; (c) calculates at least two characteristic indices representing characteristics of the image of the skin region; (d) determines a skin sensory evaluation value based on the calculated at least two characteristic indices; and (e) causes the determined skin sensory evaluation value to be displayed on the display device.

Hereinafter, a sensory evaluation device for skin and an evaluation method for skin in an embodiment according to the present invention will be described in detail with reference to the drawings.

FIG. 1(a) schematically shows a structure of a sensory evaluation device for skin in an embodiment according to the present invention. A sensory evaluation device 101 in this embodiment acquires an image of a face of a subject 24, and calculates, from the image, at least two characteristic indices representing characteristics of an image of a skin region of the face. The sensory evaluation device 101 also determines a skin sensory evaluation value from the calculated at least two characteristic indices. In this specification, the "characteristic index representing a characteristic of an image" is obtained as a result of indexing a characteristic shown in the an image of a skin region in the captured image. Specifically, the "characteristic index" is a value obtained as a result of indexing image data on blemishes, wrinkles, texture and pores of skin shown in the image, or a value obtained as a result of indexing a pixel value of the image. More specifically, the "characteristic index" is a value obtained as a result of indexing the amount of blemishes or wrinkles of the skin shown in the image; a value obtained as a result of indexing the amount of pores, which is indicated by a combination of at least one of the number, the area size and the concentration of the pores of the skin shown in the image; a value obtained as a result of indexing the fineness of the texture of the skin shown in the image; a value obtained as a result of indexing a combination of at least one of the length, the width and the depth of nasolabial folds of the skin shown in the image; a value obtained as a result of indexing the average or the dispersion of a pixel value, or the hue of the pixel, of an image of a predetermined unit block of the skin region; or a value obtained as a result of indexing the reflectance, water content, oil content and color unevenness at a surface of the skin shown in the image. The "skin sensory evaluation value" is a subjective evaluation value that is not directly found from an image. Specifically, the "skin sensory evaluation value" refers to skin clarity, skin age or impression of skin. In general, the skin sensory evaluation value is subjectively determined by an evaluator looking at the skin of a subject. The sensory evaluation device in this embodiment determines a sensory evaluation value from at least two characteristic indices on the subject as a target of evaluation, based on the correlation between the skin sensory evaluation value and at least two characteristic indices acquired from a plurality of subjects. The correlation is determined in advance by an evaluator performing an evaluation on the skin of the plurality of subjects. The evaluator is preferably a specialist in the beauty industry who is specialized in evaluating skin clarity, skin age and impression of skin, but is not limited to such a specialist and may be a general user who is not specialized in such an evaluation.

For the above-described reason, the sensory evaluation device 101 for skin shown in FIG. 1(a) includes an image capturing device 10, a light source 12, a display device 14 and a control device 18. FIG. 1(b) shows a structure of the control device 18. The control device includes a memory 18A and a computation unit 18B. The image capturing device 10 of the sensory evaluation device 101 captures an image of the face of the subject 24 to acquire an image of the face. In this process, in this embodiment, the light source 12 emitting polarized light is used in order to calculate the characteristic indices of the image more accurately.

Figure 2:
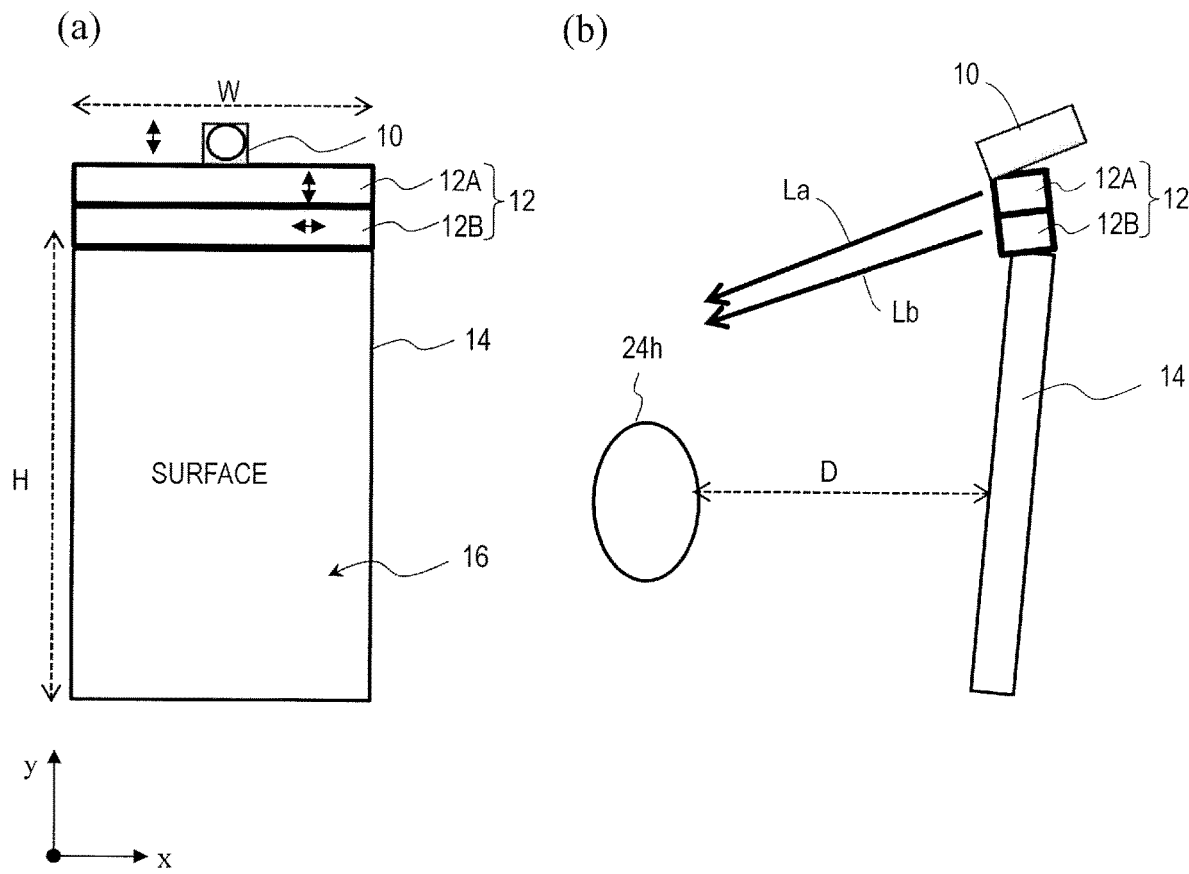
FIG. 2(a) and FIG. 2(b) are respectively a front view and a side view showing a positional arrangement of an image capturing device, a light source and a display device of the sensory evaluation device.

FIG. 2(a) and FIG. 2(b) are respectively a front view and a side view showing a positional arrangement of the image capturing device 10, the light source 12 and the display device 14 of the sensory evaluation device 101. In this embodiment, the light source 12 is provided on the display device 14, and the light source 12 includes a first light source 12A and a second light source 12B. The first light source 12A emits linearly polarized white light La having a polarization axis in, for example, a vertical direction (y direction in FIG. 2(a)), and the second light source 123 emits linearly polarized white light Lb having a polarization axis in a horizontal direction (x direction in FIG. 2(a)). A lens optical system of the image capturing device 10 includes a polarization plate having a polarization axis in, for example, the vertical direction (y direction in FIG. 2(a)). The arrows in FIG. 2(a) each show the polarization axes.

Referring to FIG. 2(b), in order to find the skin sensory evaluation value by the sensory evaluation device 101, the subject holds his/her head 24h at a position that is away from the display device 14 by, for example, about distance D, and directs his/her face toward the display device 14. The optical system of the image capturing device 10 is set such that an image of the entire face is captured with an appropriate size and an appropriate resolution in this state. The display device 14, for example, has a width W of about 30 cm and a height H of about 50 cm. The distance D is about 30 cm to about 70 cm.

The control device 18 receives data on the image from the image capturing device 10 and calculates at least two characteristic indices of the image. The control device 18 also determines the skin sensory evaluation value based on the correlation, found in advance, between the skin sensory evaluation value and the at least two characteristic indices. The display device 14 displays the captured image. The display device 14 also displays the characteristic indices of the image and the skin sensory evaluation value found by the control device 18. A screen of the display device 14 may include a user interface such as a touch panel 16 or the like. Namely, the display device 14 may be a touch screen display or the like.

The image capturing device 10 is a general video camera or digital still camera. In order to capture an image by use of polarized light, the optical system of the image capturing device 10 includes the polarization plate having a polarization axis in a predetermined direction, for example, a direction parallel to the vertical direction. The control device 18 may be a personal computer or the like, or includes a dedicated circuit or the like. In FIG. 1(a), the control device 18 and the display device 14 are shown as being separated from each other. Alternatively, the control device 18 and the display device 14 may be integrally accommodated in a casing of a tablet-type mobile information terminal or the like.

As shown in FIG. 1(a) and FIG. 1(b), the control device 18 may further include a communication unit 18C and may be connected, via a communication network 22, with a cloud service server 20 of a service provider that provides a service regarding the skin sensory evaluation. In this case, the communication unit 18C transmits the captured image, the characteristic indices of the image, the skin sensory evaluation value and the like to the cloud server 20. FIG. 1(a) shows only one sensory evaluation device 101. The cloud server 20 may be connected with a plurality of sensory evaluation devices 101.

FIG. 1(c) shows a structure of the cloud server 20. The cloud server 20 includes a database 20A, a memory 20B, a computation unit 20C and a communication unit 20D. The cloud server 20 receives, by the communication unit 20D, the captured image, the characteristic indices of the image, the skin sensory evaluation value and the like from the plurality of sensory evaluation devices 101. Based on the characteristic indices of the image received from the plurality of sensory evaluation devices 101, the cloud server 20 finds the correlation between the skin evaluation value and at least two function indices. The cloud server 20 also transmits, by the communication unit 20D, the found correlation to each of the sensory evaluation devices 101.

Hereinafter, the structure of the sensory evaluation device 101 and the skin evaluation method using the sensory evaluation device 101 will be described in detail.

Figure 3:
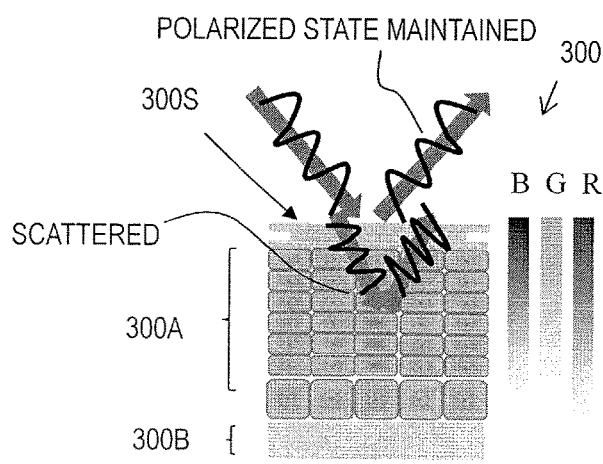
FIG. 3 schematically shows a structure inside the skin.

First, a method for measuring a characteristic index of a skin image will be described. FIG. 3 schematically shows a cross-section of human skin. The skin image includes various information on the skin such as blemishes, wrinkles, pores, nasolabial folds and the like. The characteristic index is calculated by selectively extracting such information from the skin image. As shown in FIG. 3, skin 300 includes epidermis 300A present in a depth range of about 0.06 mm or deeper to about 0.2 mm from a skin surface 300S of the skin 300 and also includes dermis 300B present deeper than the epidermis 300A. The blemishes, wrinkles, pores, and nasolabial folds have different shapes in the skin and are present at different depths of the skin 300. Therefore, the characteristic index is calculated by acquiring images of different depths of the skin and performing identification by the shape.

Information on the images from different depths of the skin is acquired by use of polarized light or color components. In the case where, for example, an image of the skin is captured using a light source that emits linearly polarized light parallel to a predetermined direction, the linearly polarized light is reflected by the skin surface 300S while the polarization direction thereof is maintained. Meanwhile, the linearly polarized light that is reflected inside the epidermis 300A goes out of the epidermis 300A while the polarization direction thereof is disturbed as a result of light scattering. Therefore, in the case where a light source that emits linearly polarized light is used and polarized light parallel to the light source is detected (condition of the parallel-polarized light), an image including a large amount of information on the skin surface and little information on the inside of the skin is acquired. By contrast, in the case where a light source that emits linearly polarized light is used and polarized light orthogonal to the light source is detected (condition of the orthogonally polarized light), an image including a large amount of information on the inside of the skin and little information on the skin surface is acquired. Namely, an image selectively including information on the inside of the skin or the information on the skin surface is acquired by using a light source that emits polarized light.

Light from the light source is incident deeper into the inside of the epidermis 300A and reflected inside as the light has a longer wavelength. Therefore, a blue (B) component of the image of the skin includes more information on the skin surface, and a red (R) or infrared component of the image of the skin includes more information on the inside of the epidermis 300A.

The characteristic indices of blemishes, wrinkles and the like may have a property of easily absorbing light of a specific wavelength region. In this case, a specific index is calculated by use of the component of light of the specific wavelength region.

Table 1 shows an example of conditions for calculating the characteristic indices.

TABLE 1

| Index | Polarized light condition | Color component condition | Filter condition |
|---|---|---|---|
| Blemishes | Orthogonally polarized light | BR difference | Threshold process |
| Wrinkles | Parallel-polarized light | BR difference | Line detection filter |
| Pores | Orthogonally polarized light | B | Point detection filter |
| Nasolabial folds | Parallel-polarized light | BR difference | Line detection filter |

Among the above-described characteristic indices, blemishes are present inside the epidermis 300A. It is known that as the blemishes are darker, a light amount difference between the blue component and the red component of light obtained from the blemishes is smaller. Therefore, the image is captured under the condition of the orthogonally polarized light, by which more information on the inside of the skin is acquired, and a pixel value difference between the blue and red components in each of pixels in the image is found and subjected to a threshold process. In this manner, the blemishes are selectively extracted from the captured image.

The wrinkles and the nasolabial folds are present in the vicinity of the skin surface 300S of the skin 300. The image is captured under the condition of the parallel-polarized light, by which more information on the skin surface is acquired, and a pixel value difference between the blue and red components in each of the pixels in the image is found. In this manner, the influence of the light reflection at the skin surface is suppressed and an image including a large amount of information on the wrinkles and the nasolabial folds is acquired. Alternatively, by processing the image by use of a line detection filter, an image including a large amount of information on the wrinkles and the nasolabial folds is acquired. In the case where the wrinkles and nasolabial folds are to be distinguished from each other, a threshold process may be further performed by the length of the detected portion.

In this example, the pixel value difference between the blue and red components is found in order to acquire an image including a large amount of information on the wrinkles and the nasolabial folds. Alternatively, a pixel value of only the blue component may be found. Still alternatively, a pixel value of a green component or any other color component may be used. The pixel value difference to be found is not limited to a pixel value difference between the blue and red components.

The pores are present in the vicinity of the skin surface 300S of the skin 300. However, under the condition of the parallel-polarized light, by which more information on the skin surface is acquired, illumination in an environment in which the sensory evaluation device 101 is used has a strong influence. In the meantime, the pores are recognizable on the image relatively easily. Especially in the case where a point detection filter is used, the pores on the image are extracted more easily. Therefore, in this embodiment, the image is captured under the condition of the orthogonally polarized light in order to suppress the influence of the illumination and calculate the characteristic index with a higher reproducibility. In addition, the blue component in each pixel of the image is extracted and the image is processed by use of the point detection filter. In this manner, an image including a large amount of information on the pores is acquired.

Table 1 shows an example of conditions for calculating the characteristic indices, and an image of a face may be acquired under any other conditions. As seen from Table 1, the characteristic indices shown in Table 1 may be calculated as being distinguished from each other without using the polarized light but using color components or filters. Therefore, although the sensory evaluation device 101 includes the light source 12 that emits polarized light in this embodiment, a sensory evaluation device may not include the light source 12 emitting polarized light.

Now, a structure of the sensory evaluation device 101 will be described in detail. FIG. 4(a) shows functional blocks of the sensory evaluation device 101. As shown in FIG. 4(a), the sensory evaluation device 101 includes an image capturing unit 32, a skin region extraction unit 34, a characteristic index calculation unit 36, a sensory evaluation value determination unit 42, a display data generation unit 44, and a display unit 45. The sensory evaluation device 101 also includes a control unit 46 controlling each of the functional blocks and an input unit 48 providing an instruction to the control unit 46. In the case where the sensory evaluation device 101 is to communicate with the cloud server 20, the sensory evaluation device 101 also includes a transmission unit 38 and a receiving unit 40.

Among the functional blocks shown in FIG. 4(a), the image capturing unit 32, the display unit 45, the control unit 46 and the input unit 48 are respectively the image capturing device 10, the display device 14, the control device 18 and the tough panel 16 shown in FIG. 1(a). The transmission unit 38 and the receiving unit 40 are realized by the communication unit 18C of the control device 18.

Functions of the skin region extraction unit 34, the characteristic index calculation unit 36 and the sensory evaluation value determination unit 42 are realized by software. Specifically, the functions of these blocks are realized by the computation unit 18B executing a program stored on the memory 18A. In accordance with the program, the computation unit 18B controls the image capturing device 10, the light source 12 and the display device 14.

When the sensory evaluation device 101 starts operating based on an instruction from a subject or an operator of the sensory evaluation device 101, first, the image capturing unit 32 captures an image of a face of the subject to acquire the image of an area including the face. The skin region extraction unit 34 extracts a skin region from the acquired image. The characteristic index calculation unit 36 calculates at least two characteristic indices of the acquired image of the skin region. The skin region is divided into a plurality of unit blocks, and the calculation of the characteristic indices is performed on a unit block-by-unit block basis.

The sensory evaluation value determination unit 42 determines a skin sensory evaluation value based on the calculated at least two characteristic indices. The sensory evaluation value is also determined on a unit block-by-unit block basis. The display data generation unit 44 generates display data usable to display the skin sensory evaluation value, found on a unit block-by-unit block basis, in association with a position of each of the unit blocks. The display unit 45 displays the generated display data.

The transmission unit 38 transmits, to the cloud server 102, the image data of the skin region extracted by the skin region extraction unit and the characteristic indices of the image. The receiving unit 40 receives, from the cloud server 102, information indicating the correlation between the skin sensory evaluation value and at least two characteristic indices, specifically, coefficients of a regression equation determined by multiple regression analysis. This information is held by the sensory evaluation value determination unit 42 and used to determine a sensory evaluation value.

The coefficients of the regression equation held by the sensory evaluation value determination unit 42 may be stored by the sensory evaluation device 101 in advance or may be acquired from the cloud server 102 before the sensory evaluation device 101 determines the sensory evaluation value.

Figure 4:
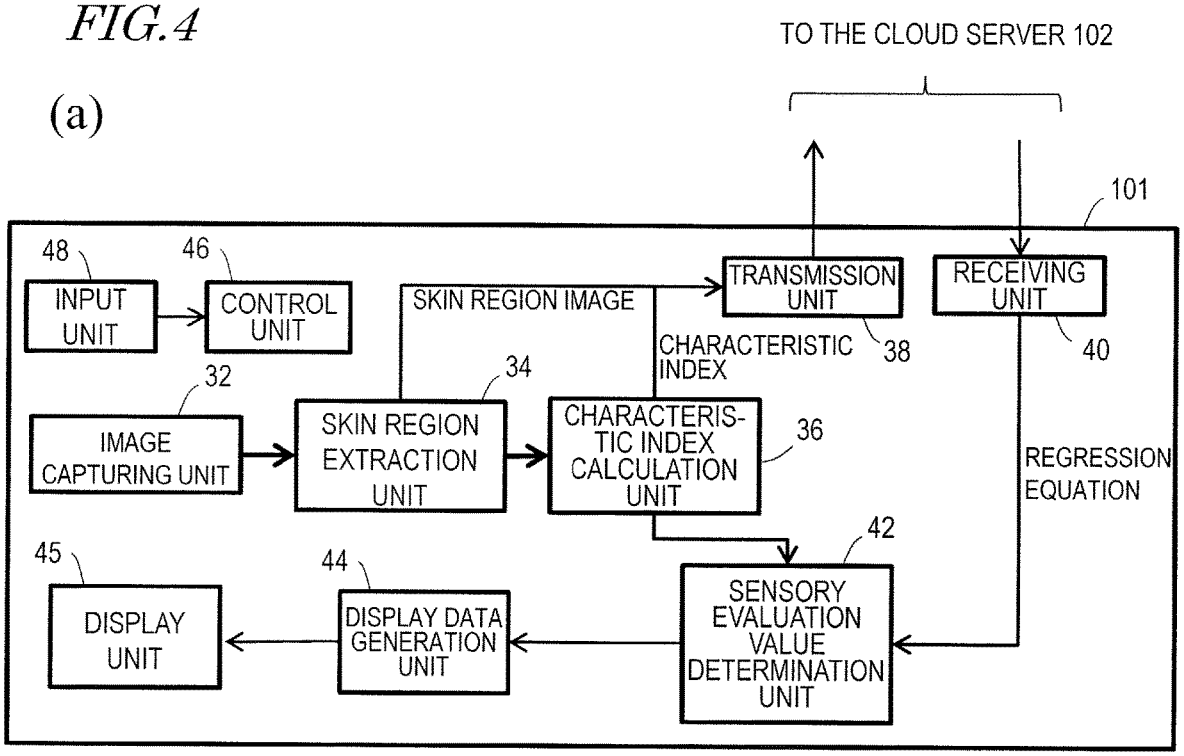
FIG. 4(a) is a functional block diagram of the sensory evaluation device.
FIG. 4(b) is a functional block diagram of the cloud server.
Figure 4:
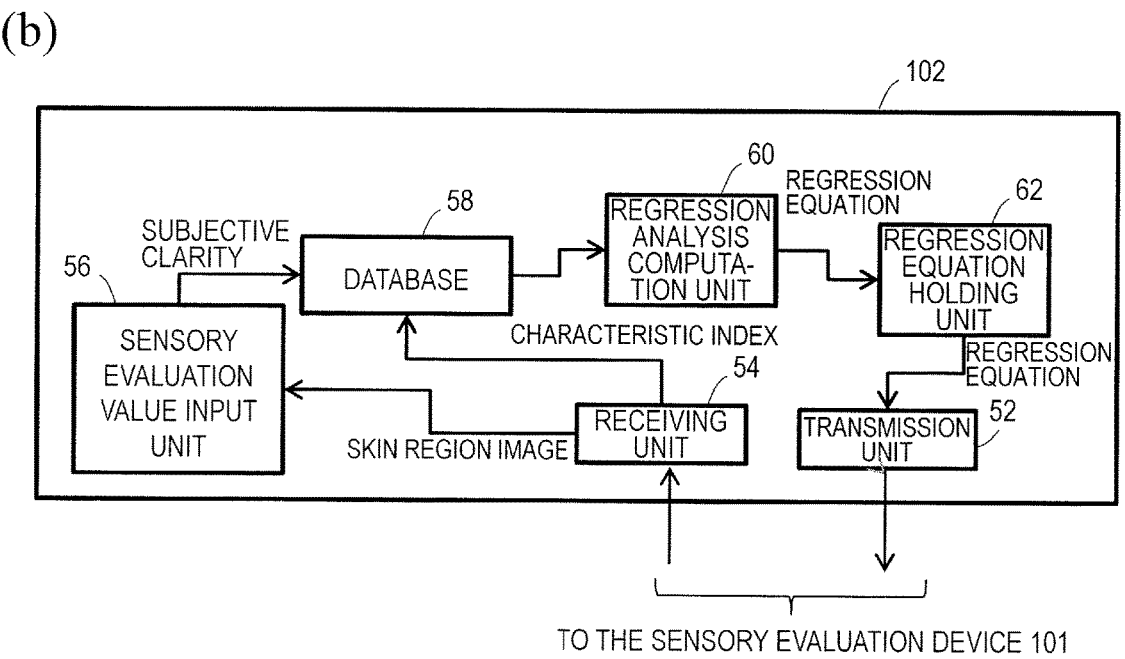

FIG. 4(*b*) shows functional blocks of the cloud server 102. The cloud server 102 includes a transmission unit 52, a receiving unit 54, a sensory evaluation value input unit 56, a database 58, a regression analysis computation unit 60, and a regression equation holding unit 62. These functional blocks are realized by software. Specifically, the functions of these blocks are realized by the computation unit 20C executing a program stored on the memory 20B of the cloud server 102.

The cloud server 102 receives the image data on the skin region and the characteristic indices of the image from the plurality of sensory evaluation devices 101 connected therewith via the communication network 22. The evaluator looks at the images of the skin regions collected to the cloud server 102, determines a sensory evaluation value of each image, and inputs the sensory evaluation value to the sensory evaluation value input unit 56. The database 58 stores the at least two characteristic indices of each image of the skin region in association with the sensory evaluation value determined for the image.

The regression analysis computation unit 60 finds the correlation between the characteristic indices and the sensory evaluation value from combinations, each of which is of the at least two characteristic indices and the determined sensory evaluation value accumulated in the database 58. Specifically, the regression analysis computation unit 60 determines, by multiple regression analysis, coefficients of the regression equation for finding the sensory evaluation value from the at least two characteristic indices. The determined coefficients of the regression equation are held by the regression equation holding unit 62 and are transmitted to the functional evaluation device 101 at a predetermined timing.

Figure 5:
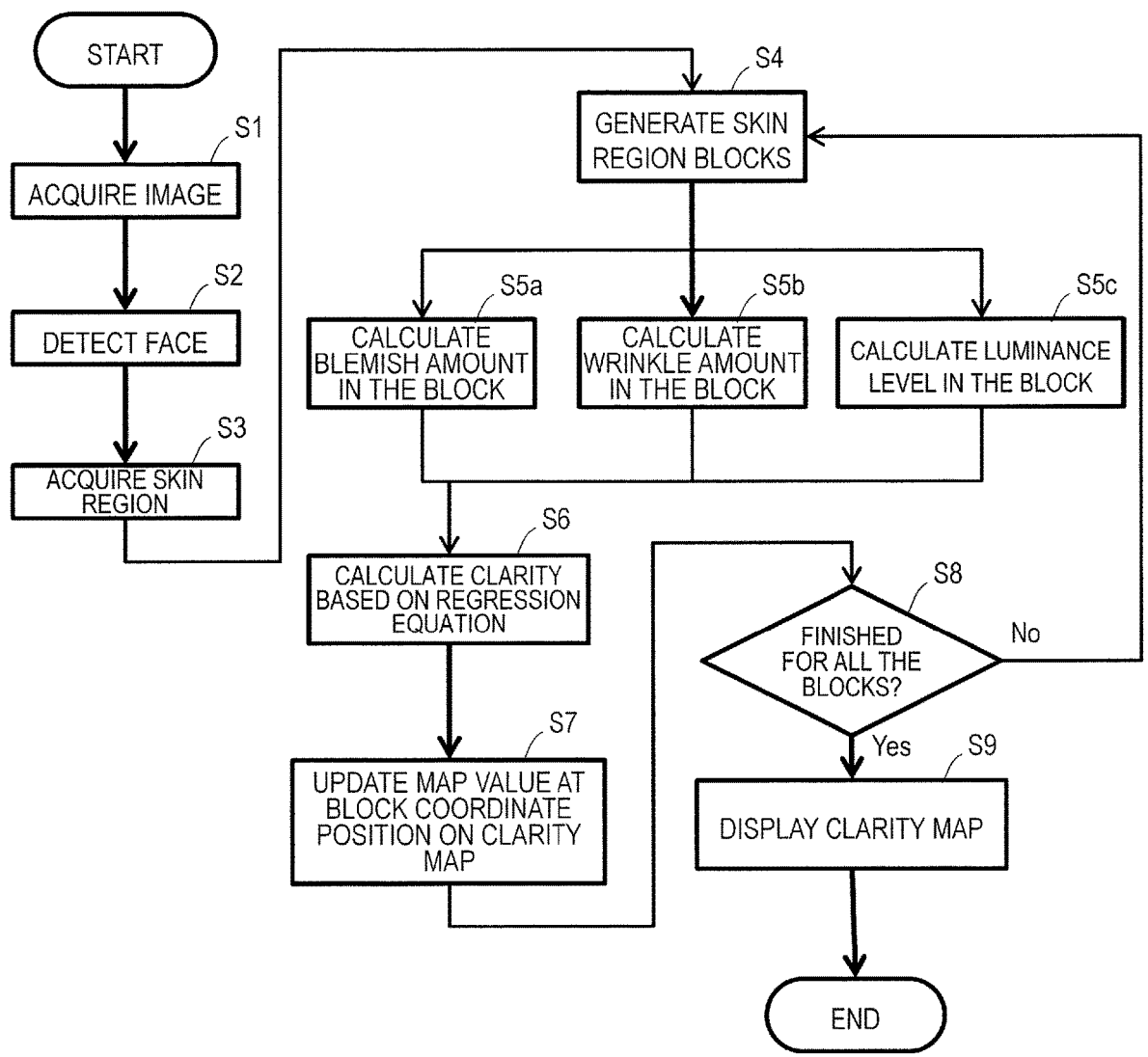
FIG. 5 is a flowchart showing a procedure of performing a skin evaluation.

FIG. 5 is a flowchart showing a procedure of skin evaluation method. With reference to FIG. 4(*a*) and FIG. 5, the skin evaluation method using the sensory evaluation device 101 will be described in more detail.

As shown in FIG. 5, first, an image of a face of a subject is acquired (step S1). In this embodiment, the image is captured by use of polarized light under the condition of the orthogonally polarized light and under the condition of the parallel-polarized light. For example, first, the first light source 12A is turned on to perform first image capturing. Then, after the first light source 12A is turned off, the second light source 12B is turned on to perform second image capturing. In this manner, the first image capturing is performed under the condition of the parallel-polarized light, and the second image capturing is performed under the condition of the orthogonally polarized light. The intensity of the light emitted by the first light source 12A may be the same as, or different from, the intensity of the light emitted by the second light source 12B. The time duration in which the light source 12A is on may be the same as, or different from, and the time duration in which the second light source 123 is on. The exposure condition of the image capturing device 10 may be the same or different for the first image capturing and the second image capturing. A first image and a second image are generated respectively by the first image capturing and the second image capturing. A calculation of a characteristic index is performed by use of one of the first image and the second image that is captured in the condition suitable to the characteristic index. The calculation of the characteristic index may be performed by use of both of the images. Hereinafter, unless it is needed to specifically distinguish the first image and the second image from each other, the first image and the second image will be collectively referred to as the "captured image of the face".

Figure 6:
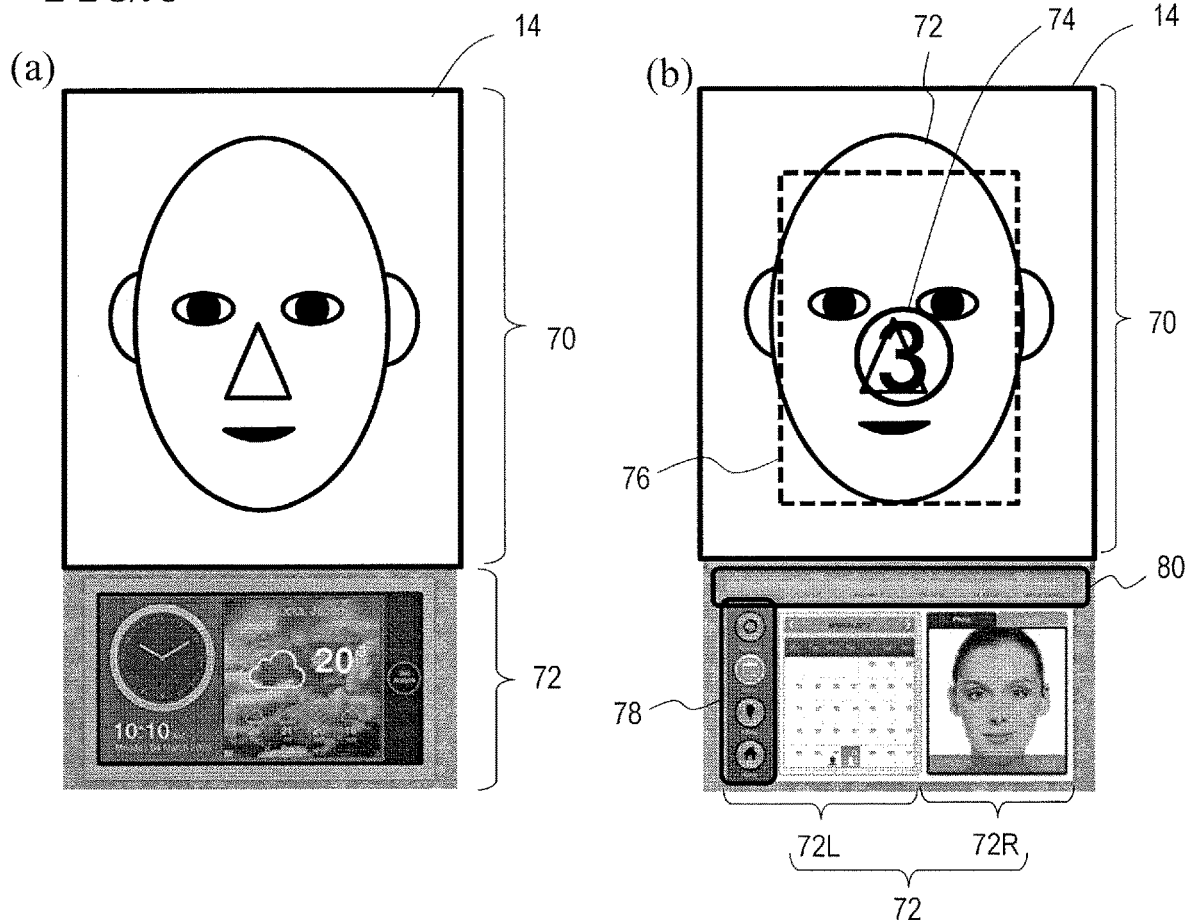
FIG. 6(a) and FIG. 6(b) each show an example of screen displayed on the display device before the sensory evaluation is performed.

FIG. 6(*a*) shows an example of initial screen displayed on the display device 14 of the sensory evaluation device 101 before the image capturing is performed. A display area of the display device 14 includes a main screen 70 having a large area size and a sub screen 72 located below the main screen 70 and having a smaller area size. In the initial screen, a captured image is displayed on the main screen 70 in real time, so that the main screen 70 acts as a digital mirror. The sub screen 72 may display, for example, a clock or information on weather forecast or the like.

FIG. 6(*b*) shows a screen immediately before the start of the image capturing. As described above, the display device 14 includes the touch panel 16 at a surface thereof. When the subject touches the touch panel 16 with his/her finger, an operation menu or a function switch menu is displayed in a top area 80 and a left side area 78 of the sub screen 72. The main screen 70 may display, for example, a guide 76 for the position of the face of the subject. Alternatively, the main screen 70 may display a mark or numerical FIG. 74 indicating the timing to perform the image capturing.

For example, in the sub screen 72, a captured image of the face is displayed in real time in a right area 72R, and a calendar is displayed in a left area 72L. The calendar may show a mark indicating that image capturing was performed in the past by use of the sensory evaluation device 101. After the display shown in FIG. 6(*b*) is provided, the image capturing is performed as described above.

Figure 7:
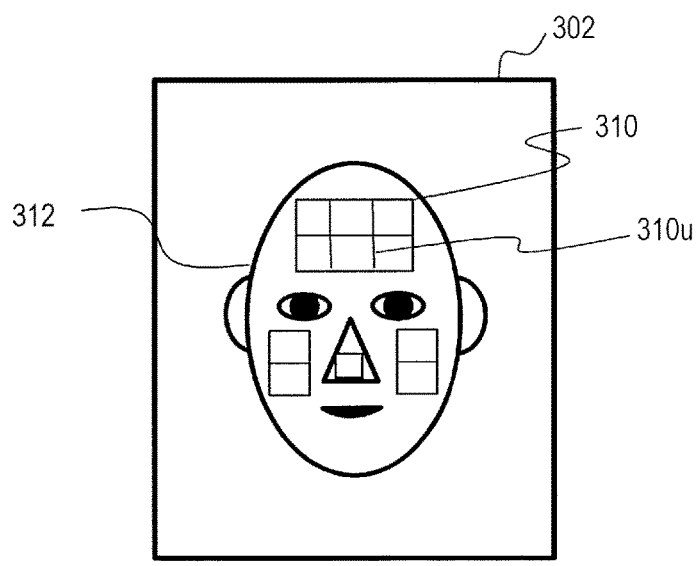
FIG. 7 shows skin regions and unit blocks in a captured image is performed.

When the image capturing of the face is finished, as shown in FIG. 7, the skin region extraction unit 34 specifies a position of a face 312 on a captured image 302. The position of the face 312 on the image 302 may be specified by use of a known face recognition and image processing technology. After the position of the face 312 is specified, areas of face parts, namely, areas of the eyes, mouth and eyebrows are removed from the area of the face 312, and a skin region 310, which is the skin, is specified on the image (step S3).

Next, the skin region extraction unit 34 divides the extracted skin region 310 to generate unit blocks 310*u* (S4). Each of the unit blocks 310*u* has a size suitable to determine the characteristic index to be calculated. For example, a unit block 310*u* has a size of 10 pixels×10 pixels. The unit blocks 310*u* may be set to partially overlap each other. In FIG. 7, the unit blocks 310*u* are shown large for easier understanding.

Next, the characteristic indices are calculated on a unit block-by-unit block basis (steps S5a, S5b, S5c). In this embodiment, a blemish amount and a wrinkle amount are calculated as the characteristic indices on a unit block-by-unit block basis. The blemish amount or the wrinkle amount is, for example, the number of pixels of an area found as being blemishes or wrinkles. The brightness of the acquired image influences the evaluation of clarity, and therefore, a luminance level is calculated on a unit block-by-unit block basis. As shown in Table 1, an image captured under the condition of the orthogonally polarized light is suitable to calculate the blemish amount. Therefore, the second image is used to calculate the blemish amount. The first image is used to calculate the wrinkle amount. The blemish amount is calculated as follows. A difference between the blue pixel value and the red pixel value of all the pixels in the unit block 310$u$ is found, and the difference is subjected to a threshold process to calculate the blemish amount. The wrinkle amount is calculated as follows. A difference between the blue pixel value and the red pixel value of all the pixels in the unit block 310$u$ is found, and the difference is subjected to a line detection filtering process. An edge portion that is found is calculated as the wrinkle amount. In addition, the luminance level of the unit block 310$u$ is calculated by use of the first image, the second image, or both of the first image and the second image.

The sensory evaluation value determination unit 42 determines clarity, namely, the sensory evaluation value, by use of the blemish amount, the wrinkle amount and the luminance level thus calculated (step S6). This will be described specifically. The correlation between the blemish amount, the wrinkle amount and the luminance level, against the clarity is found in advance by multiple regression analysis, and coefficients of the regression equation are stored on the sensory evaluation value determination unit 42 in advance. The clarity is determined by use of the regression equation. Where, for example, the blemish amount, the wrinkle amount, the luminance level and the clarity are respectively x1, x2, x3 and y, coefficients of the regression equation represented as y=a+b1*x1+b2*x2+b3*x3, namely, a, b1, b2 and b3, are stored.

The display data generation unit 44 generates image data of the image that indicates the clarity, namely, the found sensory evaluation value, and that is to be displayed in association with a coordinate position of the unit block 310$u$ in the skin region 310, for which the clarity has been found.

By repeating steps S4 through S7, levels of the clarity of all the unit blocks 310$u$ in the skin region 310 are determined (step S8).

In this embodiment, the characteristic indices are calculated on a unit block-by-unit block basis to determine the clarity levels sequentially. Alternatively, the characteristic indices of all the unit blocks 310$u$ in the skin region may be calculated, and then the clarity levels of all the unit blocks 310$u$ may be found.

The display unit 45 displays a clarity map based on the unit blocks 310$u$. The map may be displayed with color tones or gray scales corresponding to values of the clarity.

Figure 8:
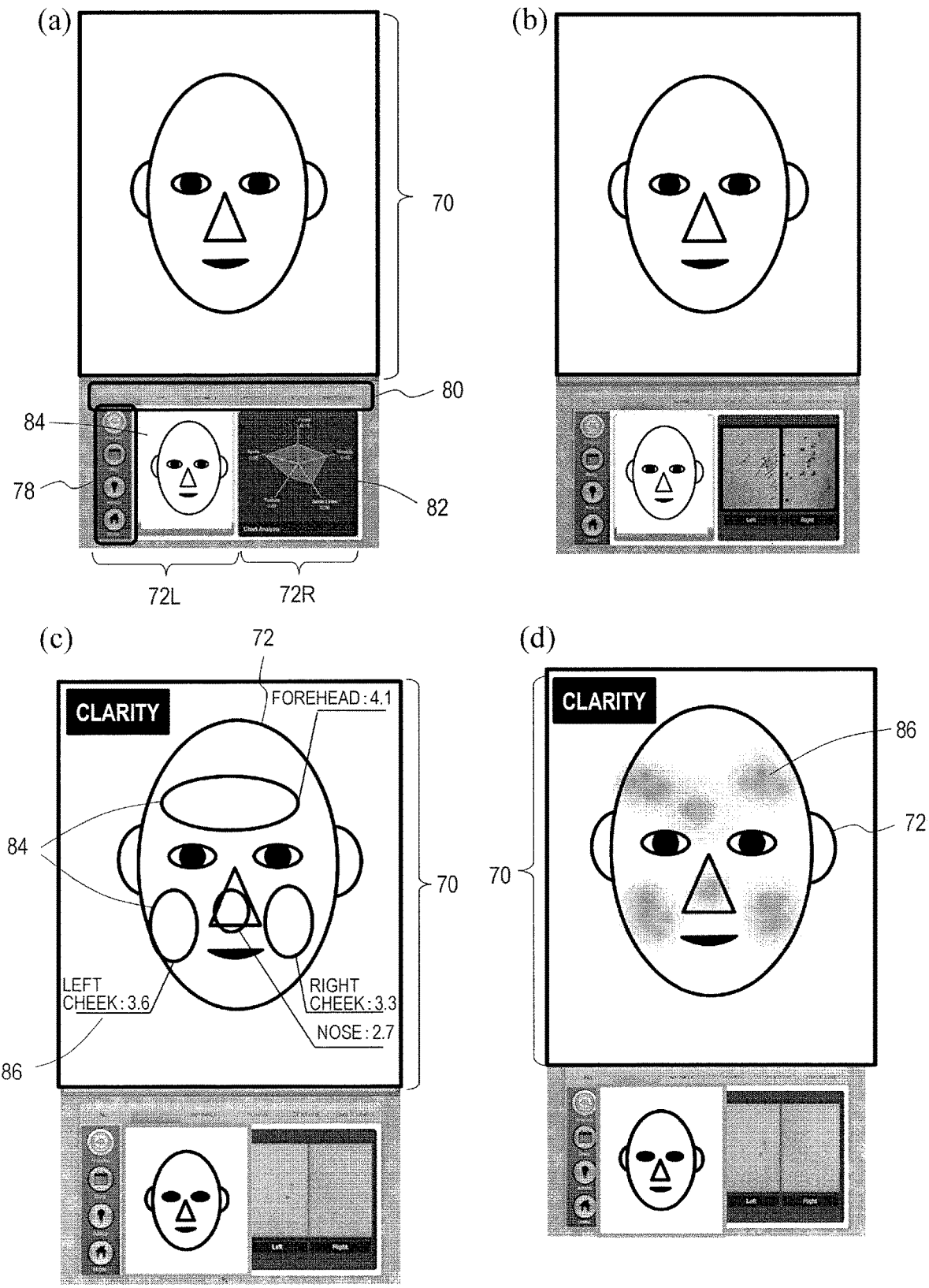
FIG. 8(a) through FIG. 8(d) each show an example of screen displayed on the display device after the sensory evaluation is performed.

FIG. 8(a) through FIG. 8(d) each show an example of screen displayed on the display device 14 after the measurement is finished. For example, when the measurement performed in the above-described procedure is finished, the screen shown in FIG. 8(a) is displayed. As shown in FIG. 8(a), the main screen 70 displays an image captured by the image capturing device 10 in real time. The right area 72R of the sub screen shows the calculated characteristic indices in the form of, for example, a radar chart. In this figure, the average characteristic indices of the entire skin region on which the measurement has been performed is displayed. In the left area 72L, the image of the face captured at the time of measurement is displayed. In the top area 80 of the sub screen 72, a menu usable to specify the position of the face is displayed. In the left side area 78, a menu usable to switch the content to be displayed or the function is displayed. The subject, for example, may touch the top area 80 or the left side area 78 of the sub screen 72 to cause a specific skin region of the face to be displayed or to change the content to be displayed.

FIG. 8(b) shows an example in which a site specified by the subject and the characteristic index specified by the subject are displayed in the right area 72R of the sub screen 72. A part of the captured image corresponding to the site specified by the subject is displayed in an enlarged state. The blemishes and the wrinkles are shown in red.

FIG. 8(c) shows an example in which the determined clarity is displayed on the main screen with an average value of each of the skin regions. In this manner, the sensory evaluation value may be shown with a numerical value.

FIG. 8(d) shows mapping display of clarity on a unit block 310$u$-by-unit block 310$u$ basis. For example, in FIG. 8(d), a unit block 86 having a low clarity level is shown with a predetermined color as overlapping the captured image.

As described above, in this embodiment, the clarity, namely, the determined sensory evaluation value, is displayed as overlapping the captured image of the face. This makes it easy to recognize which part of the entire face has a high clarity level.

Figure 9:
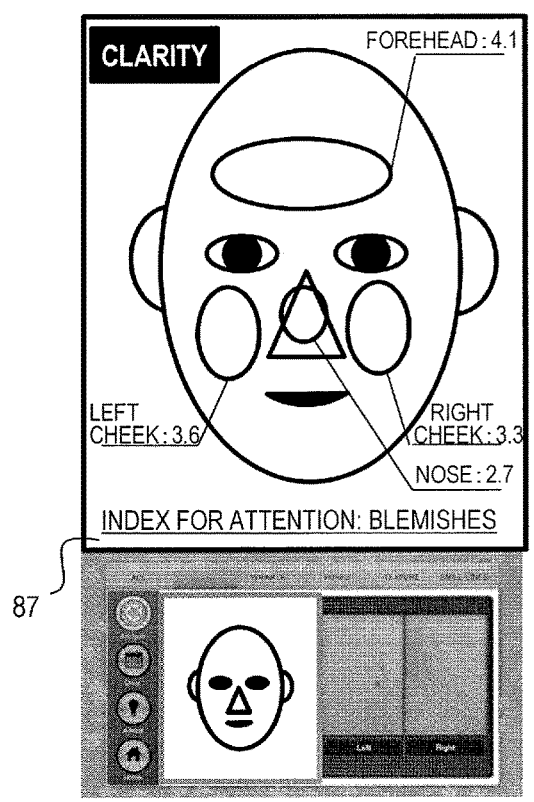
FIG. 9(a) and FIG. 9(b) each show another example of screen displayed on the display device after the sensory evaluation is performed.
Figure 9:
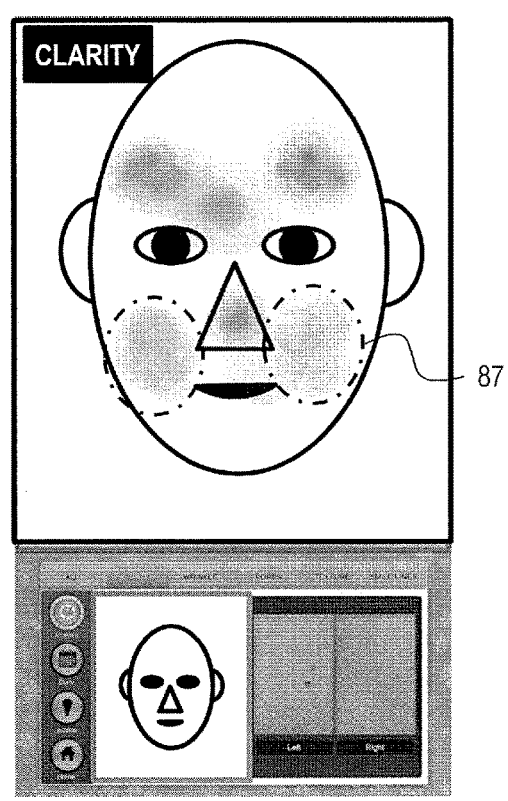

The sensory evaluation device 101 may display additional information on the display device 14 based on the resultant sensory evaluation values. FIG. 9(a) shows an example in which a characteristic index which has a larger influence on the decrease of the sensory evaluation value is shown in the case where the clarity is provided on the main screen with the average value of each skin region as shown in FIG. 8(a). FIG. 9(a) shows a display 87, which indicates that the blemish amount decreases the evaluation on the clarity.

FIG. 9(b) shows an example in which an area having a low sensory evaluation value is displayed in an emphasized manner in the case where the clarity map is displayed on a unit block 310$u$-by-unit block 310$u$ basis as shown in FIG. 8(b). In FIG. 9(b), the area having a low sensory evaluation value is emphasized with a marker 88.

In the case where a reason why the sensory evaluation is low, or the area having a low sensory evaluation value, is displayed as shown in FIG. 9(a) and FIG. 9(b), advice on how the sensory evaluation value is increased or information on cosmetics or beauty equipment usable to increase the sensory evaluation value may be further displayed in the sub screen 72. Such information on the sensory evaluation value may be, for example, stored in advance on the memory 18A of the control device 18 of the sensory evaluation device 101, or may be received by the control device 18 from the cloud server 102.

Figure 10:
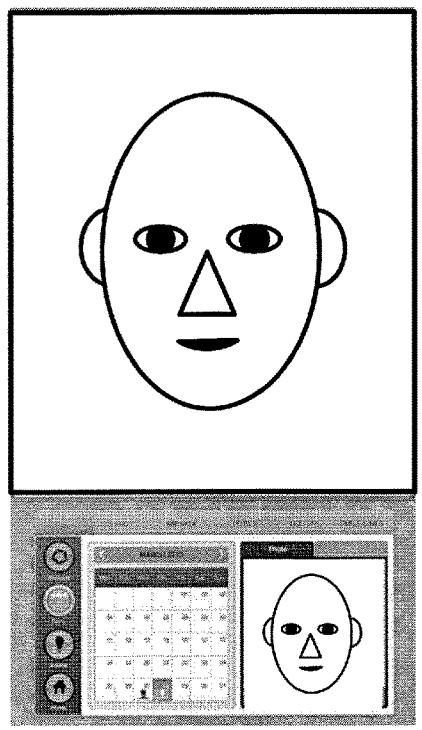
FIG. 10(a) through FIG. 10(d) each show still another example of screen displayed on the display device after the sensory evaluation is performed.
Figure 10:
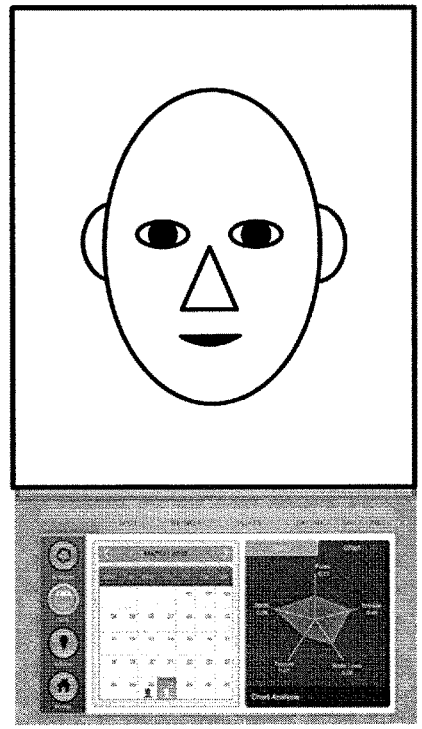
Figure 10:
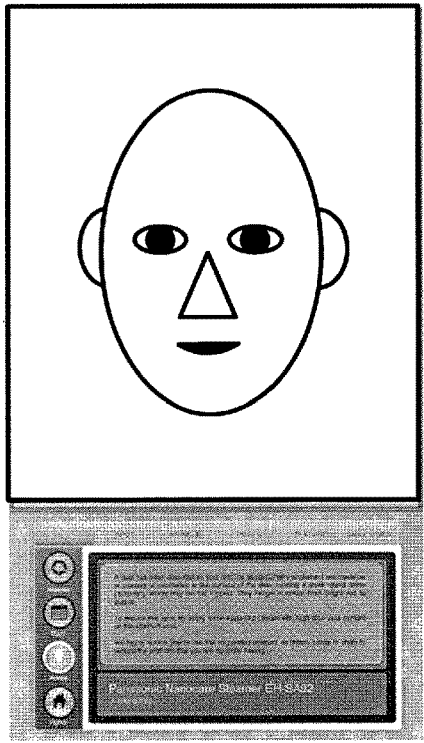
Figure 10:
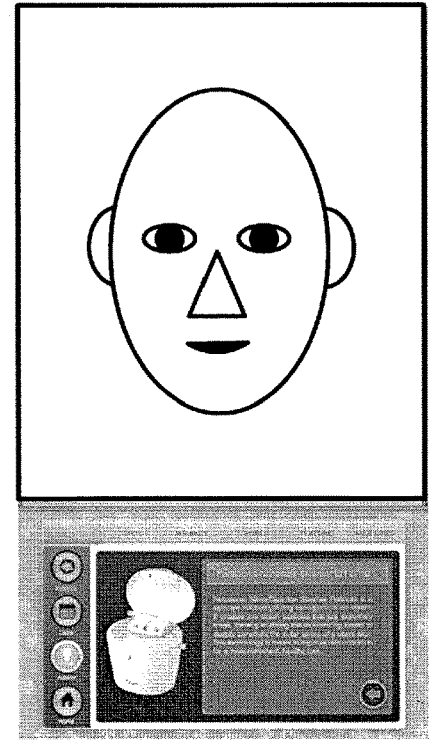

FIG. 10(a) through FIG. 10(d) each show an example of information displayed on the sub screen 72 of the display device 14. For example, as shown in FIG. 10(a), a calendar may be displayed on the sub screen. The calendar provides the information that the measurement was performed in the past. When, for example, the subject touches the corresponding information on the sub screen, the past measurement results may be displayed on the main screen 70. In this case, as shown in FIG. 10(b), a radar chart of the characteristic indices may be further displayed on the sub screen 72. As shown in FIG. 10(c), advice on skin treatment or any other beauty-related matter based on the resultant sensory evaluation values may be displayed. As shown in FIG. 10(d), information on the cosmetics or beauty equipment usable to increase the sensory evaluation value may be displayed.

Figure 11:
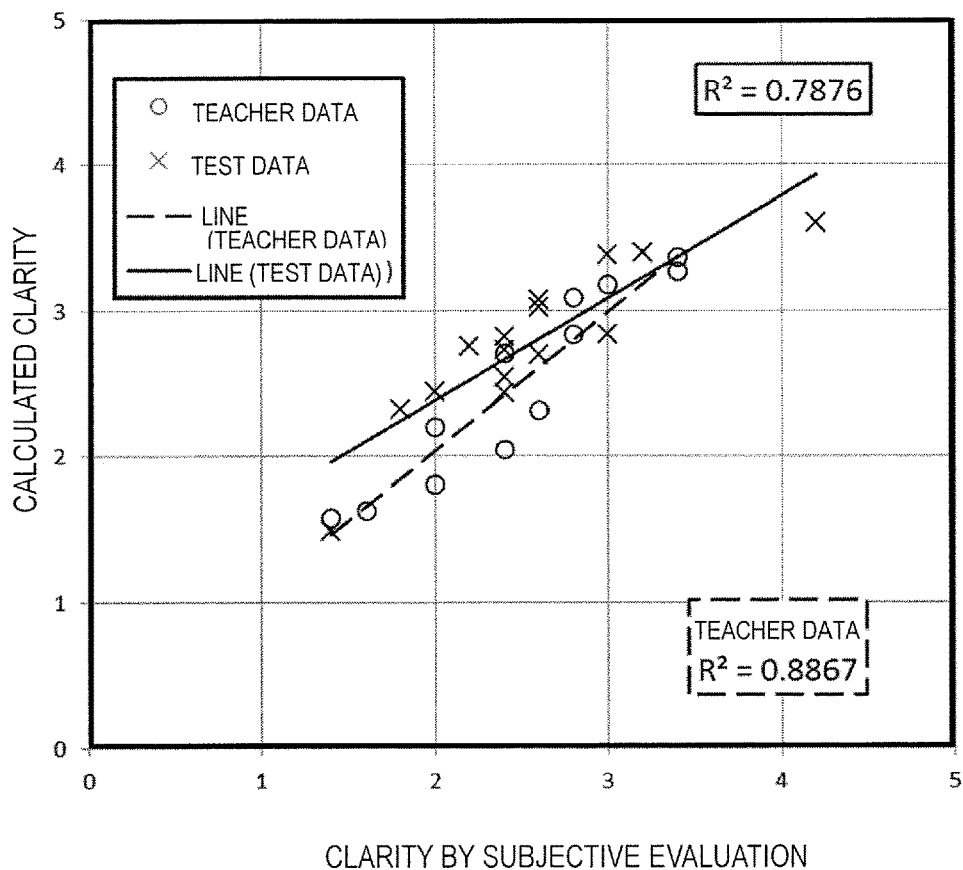
FIG. 11 shows the correlation between the clarity acquired by a subjective evaluation and the determined clarity.

FIG. 11 shows the correlation between the clarity subjectively evaluated and the clarity determined by use of the regression equation. In FIG. 11, "teacher data" is data (image of the skin region) used to determine the coefficients of the regression. "Test data" is the data, the clarity based on which was determined by the sensory evaluation device 101 by use of the determined coefficients.

In order to find the correlation, the clarity of the teacher data was also determined by the sensory evaluation device 101. The clarity of the test data was also determined by the evaluator subjectively.

As shown in FIG. 11, correlation coefficient $R^2$ between the clarity acquired from the teacher data by the subjective evaluation and the clarity of the teacher data determined by the sensory evaluation device 101 is about 0.89. This indicates that regarding the image used as the teacher data, the clarity acquired by the subjective evaluation is highly correlated with the clarity determined based on the blemish amount, the wrinkle amount and the luminance level.

Correlation coefficient $R^2$ between the clarity acquired from the test data by the subjective evaluation and the clarity of the test data determined by the sensory evaluation device 101 is about 0.79. This indicates that the regression equation acquired from the teacher data is preferably usable to estimate the clarity of an image other than the teacher data based on the blemish amount, the wrinkle amount and the luminance level at a high correlation.

Figure 12:
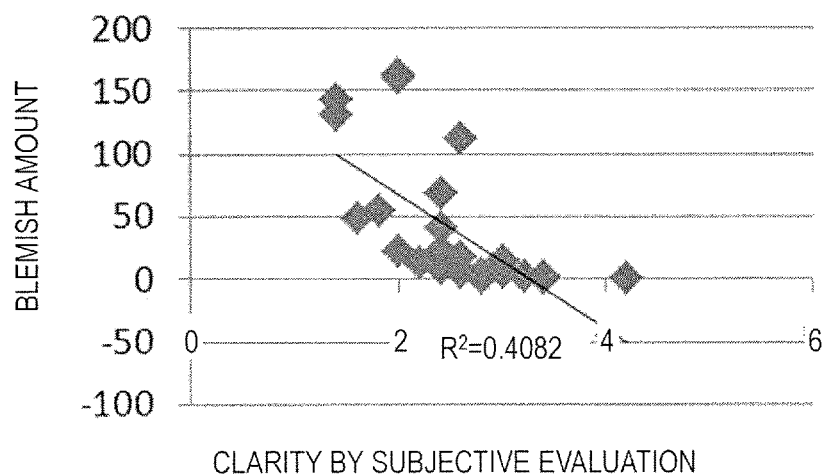
FIG. 12 shows the correlation between the clarity acquired by a subjective evaluation and the blemish amount.

FIG. 12 shows the correlation between the blemish amount and the clarity acquired by the subjective evaluation of images, the clarity of which was evaluated by the evaluator subjectively. Correlation coefficient $R^2$ between the blemish amount and the clarity acquired by the subjective evaluation is about 0.41, which is not very high. The inventor of the invention of the present application found the correlation coefficient $R^2$ between one characteristic index such as the wrinkle amount, a nasolabial fold amount or a pore amount and the clarity acquired by the subjective evaluation. Each correlation was found to be about 0.4. From this, it is seen to be difficult to estimate, at a high correlation, the skin clarity merely by use of one characteristic index such as the blemish amount, the wrinkle amount or the like directly acquired from the image of the skin region. By contrast, in the case at least two characteristic indices are used, the skin clarity is estimated at a high correlation. In this embodiment, the clarity is described as the sensory evaluation value. Alternatively, the skin age or the impression of the skin may be determined as a subjective index regarding the skin in substantially the same manner. In this case, such a sensory evaluation value may be determined based on the characteristic indices of the image of the skin also at high precision.

As described above, in this embodiment, the skin sensory evaluation value may be determined at high precision by use of at least two characteristic indices of the image of the skin.

In this embodiment, the skin sensory evaluation value may be determined by contactless measurement, and thus, in an easier manner. In addition, the skin sensory evaluation value may be determined on a site-by-site basis, namely, in units having a certain level of size. Therefore, a sensory evaluation value that is highly correlated with the sensory evaluation value acquired by an evaluation made when the face is actually looked at may be automatically found.

Figure 13:
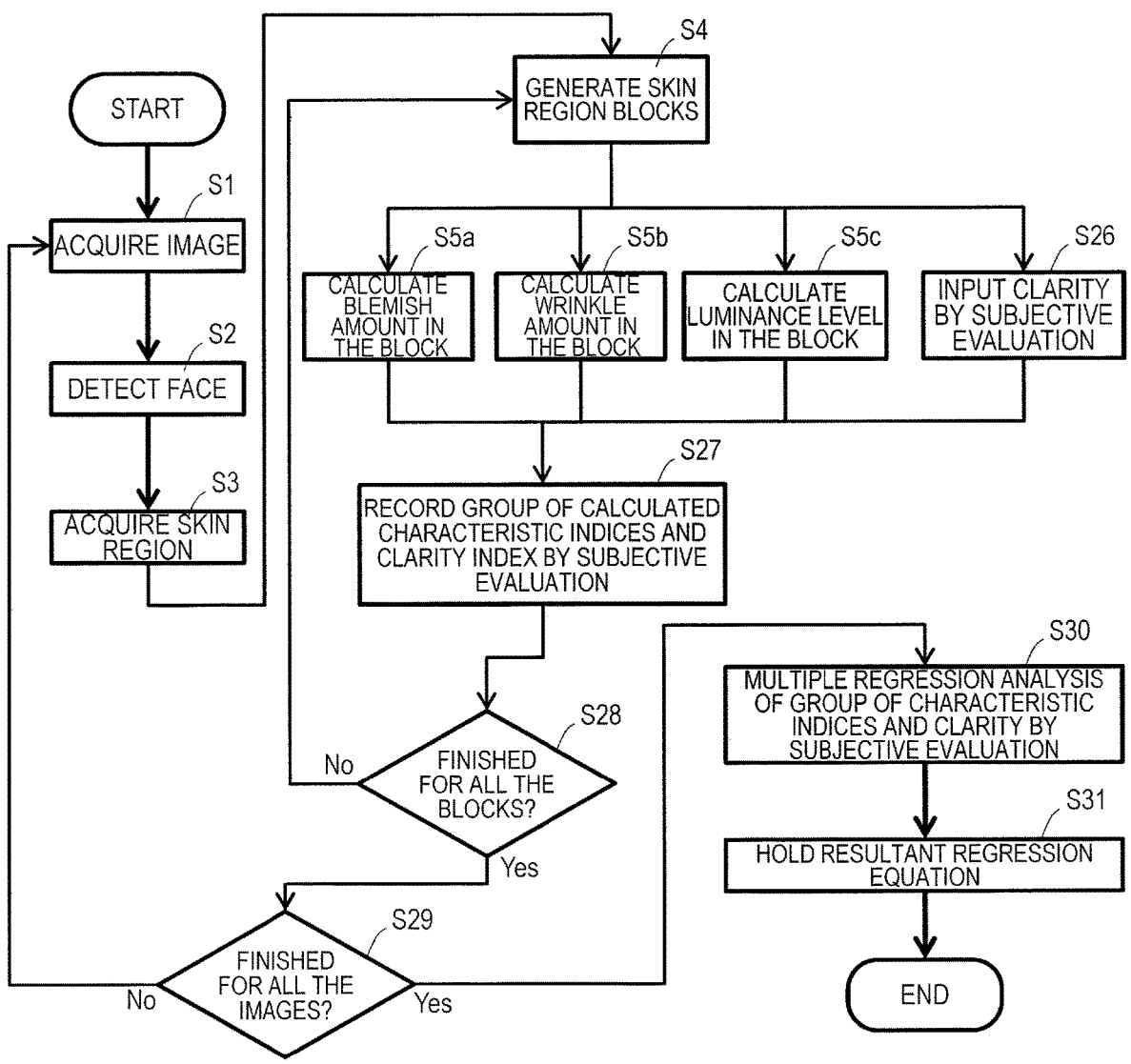
FIG. 13 is a flowchart showing a procedure of finding a regression equation by the cloud server.

Now, with reference to FIG. 4 and FIG. 13, a method for determining, by the cloud server 102, the regression equation which indicates the correlation between the characteristic indices of the image and the sensory evaluation value will be described. FIG. 13 is a flowchart showing a procedure of determining the regression equation by the cloud server 102.

The cloud server 102 may initially determine the coefficients of the regression equation and set the coefficients in the sensory evaluation device 101. Alternatively, the cloud server 102 may receive the images of the skin regions and the characteristic indices of the images sequentially from the plurality of sensory evaluation devices 101 connected with the cloud server 102, update the regression equation each time such data reaches a predetermined amount, and transmit the updated regression equation to the plurality of sensory evaluation devices 101 connected therewith.

As shown in FIG. 13, the sensory evaluation device 101 executes steps S1 through S4 and steps S5a, S5b and S5c as described above to calculate the blemish amount, the wrinkle amount and the luminance level, which are characteristic indices, of each of the unit blocks. The cloud server 102 receives such data from the sensory evaluation device 101. The cloud server 102 also receives the data of the image of the skin region from which the characteristic indices have been acquired.

The sensory evaluation value input unit 56 receives the clarity subjectively determined by the evaluator who looks at the image of the skin region (step S26). The evaluation of the clarity by the evaluator is difficult to be performed on a unit block-by-unit block basis, and therefore is performed on a skin region-by-skin region basis of the face. In this case, the unit blocks in the same skin region are associated with the same clarity level. In order to evaluate the clarity, the evaluator does not need to access the cloud server 102. For example, the cloud server 102 may transmit the data of the image of the skin region that is needed for the evaluation to an information terminal usable by the evaluator. The evaluator evaluates the clarity while looking at the image displayed on the information terminal and transmit the evaluation results, in association with the image, from the information terminal to the cloud server 102.

The input clarity is recorded on the database 58 in association with the blemish amount, the wrinkle amount and the luminance level on a unit block-by-unit block basis (step S27). This procedure is performed on all the unit blocks in the same skin region (step S28). The clarity is evaluated on all the images, the clarity of which has not been input, in substantially the same procedure, and is recorded on the database 58 (step S29).

When the clarity is evaluated on all the images, the regression analysis computation unit 60 performs multiple regression analysis on these numerical figures to find the coefficients of the regression equation in order to determine the correlation between the blemish amount, the wrinkle amount and the luminance level, against the clarity (step S30). The regression equation holding unit 62 holds the determined regression equation. Specifically, the regression equation holding unit 62 stores the coefficients of the regression equation (step S31).

The coefficients of the regression equation determined in this manner are transmitted to each of the sensory evaluation devices 101 by the transmission unit 52 of the cloud server 102. This allows each sensory evaluation device 101 to update the regression equation when necessary and to determine the clarity by use of the updated regression equation.

In this embodiment, a light source that emits polarized light is provided in order to calculate the characteristic indices with higher precision. As described above with reference to Table 1, the characteristic indices may be calculated as being distinguished from each other even with no use of the polarized light. In the case where the polarized light is not used, the sensory evaluation device in this embodiment may be realized by, for example, a mobile information device such as a smartphone, a tablet-type information device, a notebook computer or the like including a display unit and a camera located on the side of the display unit. In this case, the program executing the evaluation method for determining the skin sensory evaluation value in accordance with the procedure shown in FIG. 4 may be stored on the mobile information device and executed by a computation unit of the mobile information device to carry out the present invention as described above.

The sensory evaluation device and the evaluation method for determining a sensory evaluation value in this embodiment may be used for a skin sensory evaluation of a site other than the face, for example, a hand. In this embodiment, only the face is described as the evaluation target. Alternatively, an image of an area including the face and also the chest may be captured, and the sensory evaluation value of the neck or the chest may be measured.

INDUSTRIAL APPLICABILITY

The sensory evaluation device and the evaluation method for determining a sensory evaluation value disclosed in the present application are preferably usable for a skin sensory evaluation.

REFERENCE SIGNS LIST

10 Image capturing device
12 Light source
12A First light source
12B Second light source
14 Display device
16 Touch panel
18 Control unit
18A Memory
18B Computation unit
18C Communication unit
20 Cloud server
20A Database
20B Memory
20C Computation unit
20D Communication unit
22 Communication network
24 Subject
24h Head
32 Image capturing unit
34 Skin region extraction unit
36 Characteristic index calculation unit
38 Transmission unit
40 Receiving unit
42 Function evaluation value determination unit
44 Display data generation unit
45 Display unit
46 Control unit
48 Input unit
52 Transmission unit
54 Receiving unit
56 Function evaluation value input unit
58 Database
60 Regression analysis computation unit
62 Regression equation holding unit
70 Main screen
72 Sub screen
72L Left area
72R Right area
101 Function evaluation device
102 Cloud server

The invention claimed is:

1. An evaluation method, performed using circuitry, for determining a skin sensory evaluation value from an image captured using a camera, comprising:
   (a) acquiring an image of an area including skin of a subject using the camera;
   (b) using the circuitry, extracting a skin region from the image comprising:
     detecting a face of the subject in the image, and
     removing, from the detected face, areas containing certain parts of the face based on a position of the areas of the detected face;
   (c) calculating using the circuitry at least two characteristic indices representing characteristics of the extracted skin region based on polarized light values and/or color components of the imagined skin region;
   (d) determining a skin sensory evaluation value based on the calculated at least two characteristic indices using the circuitry; and
   (e) displaying on a display device the determined skin sensory evaluation value, wherein:
     the at least two characteristic indices include at least two of a blemish amount, a wrinkle amount, and a luminance level,
     the sensory evaluation value is an evaluation value of a skin clarity, and
     the evaluation value of the skin clarity is determined based on a correlation between the at least two characteristic indices measured on a plurality of subjects in advance and an evaluation value of the skin clarity determined by an evaluation performed on the skin of the plurality of subjects.

2. The evaluation method according to claim 1, wherein:
   in the step (b), the skin region is divided by the circuitry into a plurality of unit blocks;
   in the steps (b) and (c), the at least two characteristic indices are calculated by the circuitry to determine the skin sensory evaluation value on a unit block-by-unit block basis; and
   in step (e), the skin sensory evaluation value, found on a unit block-by-unit block basis by the circuitry, is displayed on the display device in association with a position of each of the unit blocks.

3. The evaluation method according to claim 2, wherein the step (e) displays, on the display device, the skin sensory evaluation value found on a unit block-by-unit block basis with a color tone or a gray scale suitable to the skin sensory evaluation value in association with the position of the corresponding unit block.

4. The evaluation method according to claim 1, wherein the correlation is found by multiple regression analysis.

5. The evaluation method according to claim 1, wherein information on beauty equipment or cosmetics regarding each of the calculated characteristic indices or the determined sensory evaluation value is further displayed on a display device.

6. A sensory evaluation device, comprising:
   a camera configured to acquire an image of an area including skin of a subject;

circuitry configured to:
extract a skin region from the image;
calculate at least two characteristic indices representing characteristics of the extracted skin region based on polarized light and/or color components of the imagined skin region;
determine a skin sensory evaluation value based on the calculated at least two characteristic indices; and
cause to be displayed on a display device the determined skin sensory evaluation value, wherein:
the at least two characteristic indices include at least two of a blemish amount, a wrinkle amount, and a luminance level,
the sensory evaluation value is an evaluation value of a skin clarity, and
the evaluation value of the skin clarity is determined based on a correlation between the at least two characteristic indices measured on a plurality of subjects in advance and an evaluation value of the skin clarity determined by an evaluation performed on the skin of the plurality of subjects.

7. The sensory evaluation device according to claim 6, further comprising a display; wherein:
the circuitry divides the skin region into a plurality of unit blocks;
the circuitry calculates the at least two characteristic indices on a unit block-by-unit block basis;
the circuitry determines the skin sensory evaluation value on a unit block-by-unit block basis; and
the display device displays the skin sensory evaluation value, found on a unit block-by-unit block basis, in association with a position of each of the unit blocks.

8. The sensory evaluation device according to claim 7, wherein the display device displays the skin sensory evaluation value found on a unit block-by-unit block basis with a color tone or a gray scale suitable to the skin sensory evaluation value in association with the position of the corresponding unit block.

9. The sensory evaluation device according to claim 8, wherein the correlation is found by multiple regression analysis.

10. The sensory evaluation device according to claim 6, wherein the display unit further displays information on beauty equipment or cosmetics regarding each of the calculated characteristic indices or the determined sensory evaluation value.

11. A sensory evaluation device for skin, comprising:
an image capturing device including a camera;
a control device including a non-transitory computer readable medium and a circuitry;
a display device; and
a program stored on the non-transitory computer readable medium and structured to be executable by the circuitry;
wherein the program:
(a) causes an image of an area including skin of a subject to be acquired by the image capturing device;
(b) causes a skin region to be extracted by the circuitry from the image;
(c) calculates using the circuitry at least two characteristic indices representing characteristics of the imaged skin region based on polarized light and/or color components of the imaged skin region;
(d) determines using the circuitry a skin sensory evaluation value based on the calculated at least two characteristic indices; and
(e) causes the determined skin sensory evaluation value to be displayed on the display device, wherein:
the at least two characteristic indices include at least two of a blemish amount, a wrinkle amount, and a luminance level,
the sensory evaluation value is an evaluation value of a skin clarity, and
the evaluation value of the skin clarity is determined based on a correlation between the at least two characteristic indices measured on a plurality of subjects in advance and an evaluation value of the skin clarity determined by an evaluation performed on the skin of the plurality of subjects.

12. The evaluation method according to claim 1, wherein the calculating of the at least two characteristic indices is performed based on both the polarized light values and the color components.

13. The evaluation method according to claim 1, wherein the display device acts as a digital mirror by displaying the captured image.

14. The evaluation method according to claim 1, wherein the determined skin sensor evaluation value is displayed on the display device as overlapping the detected face in the captured image.

* * * * *